US010729498B2

(12) United States Patent
    Gross

(10) Patent No.: US 10,729,498 B2
(45) Date of Patent: Aug. 4, 2020

(54) LASER ASSISTED THROMBOLYSIS

(71) Applicants: THE SPECTRANETICS CORPORATION, Colorado Springs, CO (US); Justus Gross, Laboe (DE)

(72) Inventor: Justus Gross, Laboe (DE)

(73) Assignee: THE SPECTRANETICS CORPORATION, Colorado Springs, CO (US)

(*) Notice: Subject to any disclaimer, the term of this patent is extended or adjusted under 35 U.S.C. 154(b) by 226 days.

(21) Appl. No.: 14/916,411

(22) PCT Filed: Sep. 2, 2014

(86) PCT No.: PCT/US2014/053743
    § 371 (c)(1),
    (2) Date: Mar. 3, 2016

(87) PCT Pub. No.: WO2015/034840
    PCT Pub. Date: Mar. 12, 2015

(65) Prior Publication Data
    US 2016/0228187 A1    Aug. 11, 2016

Related U.S. Application Data

(60) Provisional application No. 61/873,265, filed on Sep. 3, 2013.

(51) Int. Cl.
    *A61B 18/24* (2006.01)
    *A61M 25/00* (2006.01)
    (Continued)

(52) U.S. Cl.
    CPC ....... *A61B 18/245* (2013.01); *A61M 25/0026* (2013.01); *A61B 18/14* (2013.01);
    (Continued)

(58) Field of Classification Search
    CPC ................. A61B 18/245; A61M 25/0026
    (Continued)

(56) References Cited

U.S. PATENT DOCUMENTS 4,988,163 A * 1/1991 Cohen .................... B23K 26/06
                                                        385/31
5,273,526 A   12/1993 Dance et al.
                    (Continued)

FOREIGN PATENT DOCUMENTS

WO    1993014689 A2    8/1993
WO    1998040123 A1    9/1998
                (Continued)

OTHER PUBLICATIONS

International Search Report and Written Opinion issued in PCT/US2014/053743, dated Dec. 19, 2014, 18 pages.

*Primary Examiner* — Phillip A Gray

(57) ABSTRACT

The present disclosure relates to methods and systems for removing a vascular obstruction in a subject using a combination of thrombolytic and laser ablation therapy. Treatment methods include positioning a catheter adjacent to an obstruction within a vessel of a subject. A portion of the obstruction may be ablated by delivering laser energy through the optical fibers to the distal end of the catheter, where the optical fibers are exposed, and circulating a fluid containing one or more thrombolytic agents to a remaining portion of the obstruction for a predetermined amount time. Fluid containing one or more thrombolytic agents capable of dissolving a remaining portion of the obstruction may be circulated through the fluid delivery lumen and removed through the fluid removal lumen.

18 Claims, 5 Drawing Sheets

(51) Int. Cl.
*A61B 18/22* (2006.01)
*A61B 18/00* (2006.01)
*A61N 7/00* (2006.01)
*A61B 18/18* (2006.01)
*A61B 18/14* (2006.01)

(52) U.S. Cl.
CPC ............ *A61B 2018/0022* (2013.01); *A61B 2018/0041* (2013.01); *A61B 2018/00285* (2013.01); *A61B 2018/00577* (2013.01); *A61B 2018/00982* (2013.01); *A61B 2018/1861* (2013.01); *A61B 2018/2211* (2013.01); *A61B 2218/001* (2013.01); *A61M 2025/004* (2013.01); *A61M 2025/0031* (2013.01); *A61N 7/00* (2013.01)

(58) Field of Classification Search
USPC .................................... 604/20, 500
See application file for complete search history.

(56) References Cited

U.S. PATENT DOCUMENTS

| | | |
|---|---|---|
| 5,938,595 A | 8/1999 | Glass et al. |
| 6,022,336 A * | 2/2000 | Zadno-Azizi ......... A61B 17/22 604/101.05 |
| 6,149,596 A | 11/2000 | Bancroft |
| 6,547,779 B2 | 4/2003 | Levine et al. |
| 6,706,011 B1 | 3/2004 | Murphy-Chutorian et al. |
| 2002/0133111 A1 | 9/2002 | Shadduck |
| 2012/0035530 A1 | 2/2012 | Wang |

FOREIGN PATENT DOCUMENTS

| | | |
|---|---|---|
| WO | 1998048882 A1 | 11/1998 |
| WO | 2003057060 A1 | 7/2003 |

* cited by examiner

LASER ASSISTED THROMBOLYSIS

CROSS-REFERENCE TO RELATED APPLICATION

This application claims the benefit of U.S. Provisional Patent Application Ser. No. 61/873,265, filed on Sep. 3, 2013, which is hereby incorporated herein by reference in its entirety for all that it teaches and for all purposes.

FIELD

The present disclosure relates generally to medical devices and, in particular, to methods and systems for removing a vascular obstruction in a subject using a combination of thrombolytic and laser ablation therapy.

BACKGROUND

The formation of vascular obstructions in a subject, such as a blood clot or thrombus, can obstruct the flow of blood through the circulatory system and cause significant health problems. Vascular obstructions can form, for example, upon a blood vessel being injured after which the subject's body responds by forming a clot made of thrombocytes and fibrin at the injury site. In other instances, vascular obstructions can form independently of injury to a vessel. For instance, the subject may be genetically predisposed to form blood clots, or blood clots may form as a result of dietary and/or lifestyle choices. Regardless of the etiology, the formation of a vascular obstruction in a subject remains a significant health concern.

For example, deep vein thrombosis (DVT) can is a blood clot that forms in a vein deep in the body. DVT has led to the hospitalization of over 600,000 people in the United States annually. The most serious complication of DVT, referred to as pulmonary embolus, contributes to the death of approximately 200,000 people in the United States annually, and is the third most common cause of cardiovascular related mortality after myocardial infarction and stroke. Symptoms of DVT are collectively referred to as post-thrombotic syndrome (PTS), and include leg heaviness, tiredness, cramping and ulceration.

Conventional therapy for the treatment of vascular obstructions like those that occur with DVT include the administration of anticoagulation medication. However, this method of treatment is based upon a single clinical trial from 1960 in combination with several subsequent observational trials, has changed little since that time. Anticoagulation therapy generally includes treatment with heparin or, more recently, low-molecular-weight heparin, followed by three months of oral anticoagulation therapy. Rather than causing significant fibrinolytic activity, the treatment relies instead on a subject's own fibrinolytic mechanisms (e.g., urokinase activity); thus, anticoagulation therapy generally does not result in the removal or destruction of the thrombus.

Other therapies have emerged to treat vascular obstructions, and some of the most widely used therapies include thrombolytic therapy and catheter directed thrombectomy (CDT). Thrombolytic therapy, or thrombolysis, involves the administration of pharmacological agents that generally result in the increased activation or production of plasmin, a proteolytic enzyme that breaks down fibrin located in a blood clot, thereby dissolving it. Despite the widespread access to thrombolytic therapy, as well as its ability to be rapidly and conveniently administered, drawbacks of thrombolytic therapy include a patency ceiling, low clinical efficacy, and hemorrhagic risk.

Vascular obstructions can also be removed via the use of various thrombectomy procedures. The rationale for this more active removal of a thrombus relies on multiple observations that doing so improves luminal patency, restores valvular function and has the potential to reduce the severity of PTS. Despite these advantages, thrombectomy procedures are usually emergency surgical procedures, often viewed as a last resort, because they generally involve a risk of distal embolization and blood loss during extraction of the thrombus. Additionally, a highly adherent thrombus can be very difficult to remove without causing potential damage to the surrounding vessel.

Therefore, given that thrombolysis often fails to completely remove vascular obstructions, and given that thrombectomy procedures often cause tissue damage in surrounding blood vessels, there is need for more efficacious methods and systems for treating thrombosis.

SUMMARY

These and other needs are addressed by the various aspects, embodiments, and configurations of the present disclosure.

In various embodiments, a method of treating thrombosis, such as a deep vein thrombosis (DVT), in a subject is provided. Embodiments of the method include positioning a catheter comprising a proximal end, a distal end, a plurality of optical fibers, a fluid delivery lumen and a fluid removal lumen, adjacent to an obstruction within a vessel of the subject. The plurality of optical fibers extends through at least a portion of the catheter to the distal end, where the plurality of optical fibers are exposed. Embodiments of the method include ablating at least a portion of the obstruction by delivering laser energy through the plurality of optical fibers to the distal end of the catheter, and circulating a fluid to a remaining portion of the obstruction for a predetermined amount time. Embodiments of the method include circulating the fluid through the fluid delivery lumen and the fluid removal lumen, wherein the fluid includes one or more thrombolytic agents capable of dissolving the remaining portion of the obstruction.

The methods generally include ablating at least a portion of the obstruction prior to circulating the fluid. In other embodiments, the method includes ablating at least a portion of the obstruction simultaneously with circulating the fluid. Embodiments also include performing the ablation procedure for between about 2 minutes and about 10 minutes, and in some cases, for about 5 minutes. Embodiments also include circulating the fluid such that it is in contact with the remaining portion of the obstruction for between about 10 minutes and about 60 minutes. In some cases, the fluid is in contact with the remaining portion of the obstruction for about 30 minutes.

The fluid may include one or more thrombolytic agents, for example, tissue plasminogen activator (tPA), heparin, alteplase, anistreplase, kabikinase, prourokinase, reteplase, rokinase, streptokinase, tenecteplase and urokinase. In some cases, the one or more thrombolytic agents is tissue plasminogen activator (tPA), which is administered to the subject at a dosage between about 0.5 and about 1.2 milligrams per kilogram (mg/kg) of the subject's body weight. In other cases, tPA is administered at a dosage of about 0.9 mg/kg of the subject's body weight.

In certain embodiments, a system for treating thrombosis, such as a deep vein thrombosis (DVT), in a subject is provided. Embodiments include the use of a laser ablation catheter that includes a proximal end, a distal end, a plurality of optical fibers, a fluid delivery lumen, and a fluid removal lumen, wherein the plurality of optical fibers extend through at least a portion of the catheter to the distal end, and wherein the plurality of optical fibers are exposed at the distal end of the catheter. Embodiments of the system also include positioning the distal end of the catheter adjacent to an obstruction in a vessel of a subject to facilitate ablation of at least a portion of the obstruction by delivering laser energy through the plurality of optical fibers to the distal end of the catheter. Embodiments of the system also include circulating a fluid that includes one or more thrombolytic agents through the fluid delivery lumen and the fluid removal lumen such that it contacts a remaining portion of the obstruction for a predetermined amount of time.

The system generally includes ablating at least a portion of the obstruction prior to circulating the fluid. In other embodiments, the system includes ablating at least a portion of the obstruction simultaneously with circulating the fluid. Embodiments also include performing the ablation procedure for between about 2 minutes and about 10 minutes, and in some cases, for about 5 minutes. Embodiments also include circulating the fluid such that it is in contact with the remaining portion of the obstruction for between about 10 minutes and about 60 minutes. In some cases, the fluid is in contact with the remaining portion of the obstruction for about 30 minutes.

The fluid may include one or more thrombolytic agents, for example, tissue plasminogen activator (tPA), heparin, alteplase, anistreplase, kabikinase, prourokinase, reteplase, rokinase, streptokinase, tenecteplase and urokinase. In some cases, the one or more thrombolytic agents is tissue plasminogen activator (tPA), which is administered to the subject at a dosage between about 0.5 and about 1.2 milligrams per kilogram of the subject's body weight. In other cases, tPA is administered at a dosage of about 0.9 milligrams per kilogram of the subject's body weight.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

"Ablation" as used herein can refer to various means of focusing energy to a desired location, including, but not limited to, laser ablation, radiofrequency ablation (RF ablation), ultrasonic ablation, and microwave ablation. "Ablation" as used herein also includes various means of using mechanical energy, such as cutting. "Ablation" as used herein can also refer to combinations of laser ablation, RF ablation, ultrasonic ablation, microwave ablation and ablation using mechanical means.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The terms "determine," "calculate," and "compute," and variations thereof, as used herein, are used interchangeably and include any type of methodology, process, mathematical operation or technique.

A "laser emitter" refers to an end portion of a fiber or an optical component that emits laser light from a distal end of the catheter towards a desired target, which is typically tissue.

An optical fiber (or laser active fiber) is a flexible, transparent fiber made of an optically transmissive material, such as glass (silica) or plastic, which functions as a waveguide, or "light pipe," to transmit light between the two ends of the fiber.

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1A:
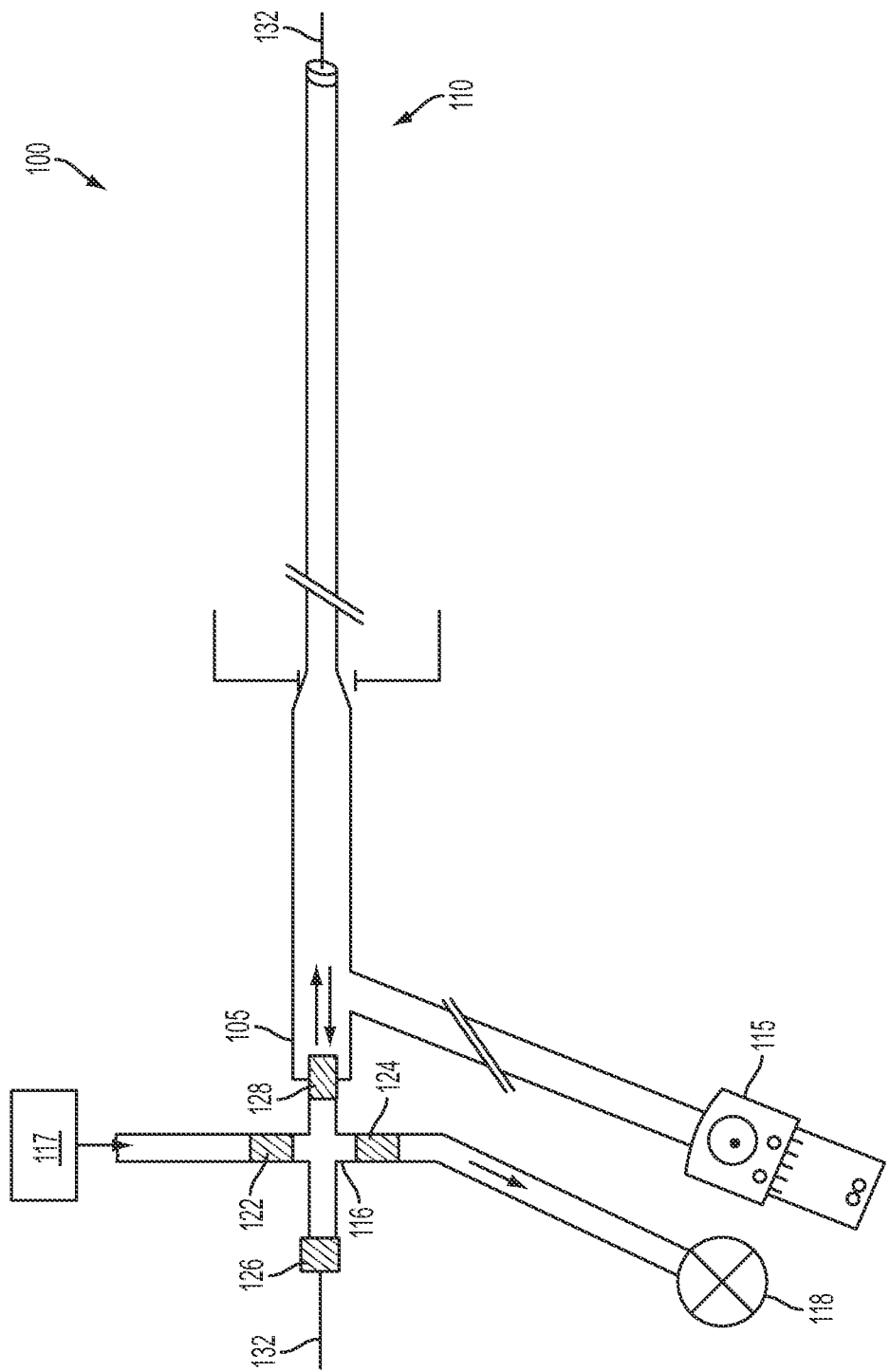
FIG. 1A is a top view of a laser catheter, according to an embodiment of the present disclosure.

The present disclosure relates generally to medical devices and, in particular, to methods and systems for removing a vascular obstruction in a subject using a combination of thrombolytic and laser ablation therapy.

Catheter assemblies, systems and procedures described herein are designed for treating vascular obstructions, including a thrombosis, such as DVT. One type of catheter assembly may include a laser catheter to treat the obstruction. The laser catheter may be used with a guidewire. For example, a procedure may include advancing a guidewire a safe distance into and beyond an obstruction. A diagnostic device (e.g., an optical or ultrasound imaging guidewire) can also be used to allow the physician to know the length and direction of the catheter advancement. The physician may then advance the laser catheter over the guidewire (through the guidewire lumen in the laser catheter). Once the catheter is adjacent the vascular obstruction, the physician may activate the laser catheter, thereby ablating a portion of the obstruction. The physician may continue to penetrate a safe distance into the obstruction. The physician may also retract or advance the laser catheter over the guidewire further through the obstruction.

Catheter assemblies, systems and procedures described herein may also facilitate the rapid exchange of devices through the distal portion of the catheter to provide an efficient "back-and-forth" exchange between a diagnostic device, a guidewire, or some other therapeutic device. This may be accomplished by having multiple lumens (i.e., two or more) in a proximal region of the catheter. This allows a relatively short retraction/advancement distance between the proximal regions and the distal tip of the catheter facilitating the rapid exchange of devices in the catheter.

The devices alternated in the distal region of the catheter may include guidewires, diagnostic devices, therapeutic devices, and fluid delivery devices. A diagnostic device may provide the catheter operator with information to locate the positions of device in relation to the obstruction and the vessel walls, among other functions. A therapeutic device may perform actions on the obstruction to help relieve the blockage of the vessel by the obstruction, among other functions. Therapeutic devices may also include guidewires and steering wires that help guide at least a portion of the catheter. Fluid devices may also be used to eject fluid to treat the obstruction itself (e.g., thrombolysis), or fluids can be used to wash the area of the vessel around the obstruction.

Embodiments also include the placement of optical fibers eccentric to the distal region of the catheter to deliver light to the distal tip while a therapeutic device is present in the distal region. The optical fibers may be used to deliver light to the site of the obstruction for purposes of material ablation, as well as to transmit images from the treatment site.

The optical fibers may extend from an optical coupling element that reversibly couples the optical fibers to a light source, such as an excimer laser. The fibers may traverse the length of the catheter assembly and terminate at the distal end of the catheter. The distal ends of the fibers may be positioned radially around the entire circumference of the distal region of the catheter, or they may partially surround this region. For example, the fibers may surround half the distal region in a hemispherical distribution. The light transmitted by the optical fibers light energy may be used to ablate or penetrate the obstruction at a treatment site. The fibers may be used to provide images and other information to the catheter operator.

The assemblies and systems of the present disclosure may also be used to ablate and/or penetrate a portion of the obstruction. This may include using a guidewire to advance the catheter to a site proximate to a portion of the obstruction, and applying light energy from optical fibers surrounding the distal region to the obstruction. A fiber optic cable advanced through the distal lumen may apply light energy in addition to (or in lieu of) the light from the optical fibers. Following an initial application of light energy, an imaging device may be advanced though the distal lumen to determine the extent of the ablation or penetration and where to further advance the catheter tip (if necessary).

Referring to FIG. 1A, one embodiment of the laser catheter 100 is shown. Laser catheter 100 may include a proximal end 105 and a distal end 110. The proximal end 105 of the laser catheter 100 may comprise of one or more couplers. For example, the proximal end 105 of laser catheter 100 may comprise a fiber optic coupler 115, which connects the fiber optic cables within the laser catheter 100 to a light source (e.g., an excimer laser), or another power source for operating diagnostic and therapeutic devices advanced through the laser catheter 100. The proximal end 105 of laser catheter 100 may also comprise a fluid coupler 116, which connects the laser catheter to a fluid source 117 and a fluid collector 118 via respective ports in the fluid coupler 116. The fluid coupler 116 may also include a guidewire lumen (FIGS. 1D-E, ref no. 130) for insertion of a guidewire 132 at the proximal end of the laser catheter 100. Although the fluid coupler 116 is illustrated as a separate component in FIG. 1A, the fluid coupler may be integral with the laser catheter 100.

The fluid coupler 116 depicted in FIG. 1A may have at least four ports: a fluid delivery port 122; a fluid evacuation port 124; a guidewire port 126; and a port 128 that connects to the proximal end 105 of the laser ablation catheter 100. The port 128 is designed such that it is in fluid communication with the fluid entering the fluid delivery port 122 and the fluid exiting the fluid evacuation port 124. Accordingly, the fluid coupler 116 may have separate channels for the fluid delivery port 122 and the fluid evacuation port 124 to communicate with the port 128. Similarly, the guidewire port 126 is designed to be in communication with port 128, and the fluid coupler 116 may, therefor, have an additional, separate channel for the guidewire to pass through the fluid coupler 116 from the guidewire port 126 to the port 128.

The laser catheter 100 may also include a plurality of lumens that are aligned with the channels within the port 128. That is, the laser catheter 100 may include a fluid delivery lumen, a fluid removal or evacuation lumen, and a guidewire lumen that extend from the proximal end 105 of the laser catheter 100 to the distal end 100 or adjacent thereto. The laser catheter may also include additional lumens to allow the operator to selectively use and exchange multiple therapeutic devices (e.g., guidewires, laser-assisted guidewires, imaging devices, steering wires, and atherectomy devices, fluid delivery devices, fluid removal devices, etc.) without having to retract them completely from the catheter. For example, the laser catheter 100 depicted in FIG. 1A is an over-the-wire configuration, thereby allowing the guidewire 132 to enter the proximal end 105 of the laser catheter 100. The laser catheter 100, however, may have an alternative configuration, such as a rapid exchange design, that allows for guidewires and/or other instruments to be inserted into and through the shaft of the laser catheter distally of the proximal end.

Figure 1B:
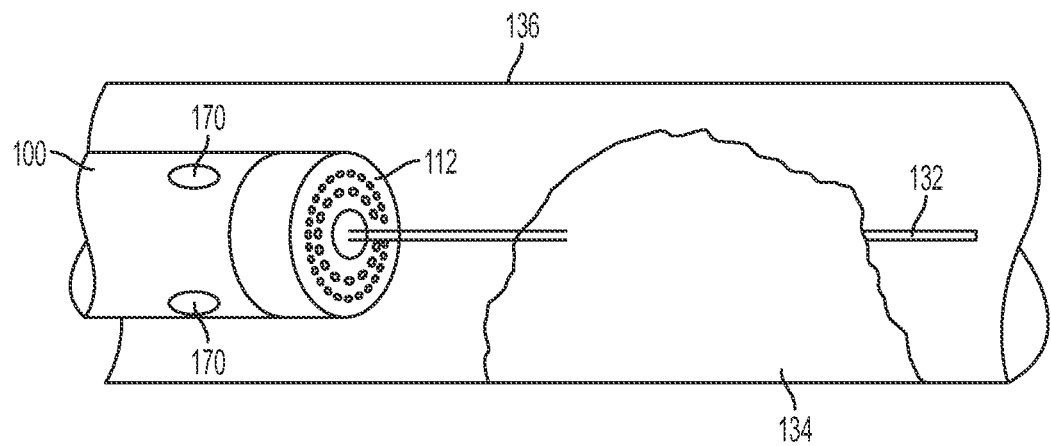
FIG. 1B is a perspective view of the distal end of a laser catheter positioned within a blood vessel and adjacent a thrombus prior to ablating the thrombus, according to an embodiment of the present disclosure.
Figure 1C:
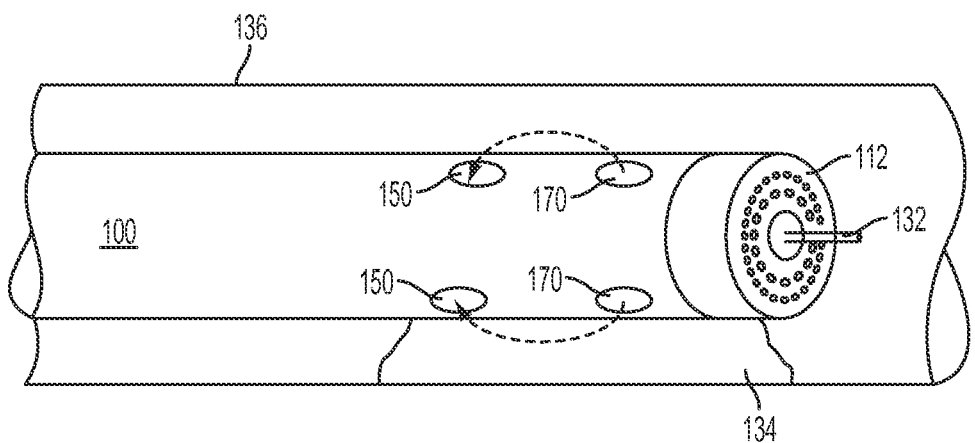
FIG. 1C is a perspective view of the distal end of a laser catheter positioned within a blood vessel and adjacent a thrombus after ablating the thrombus, according to an embodiment of the present disclosure.

Referring to FIG. 1B, there is depicted a perspective view of the distal end 110 of an embodiment of laser catheter 100 within a blood vessel 136. The distal face 112 or laser emitter of the laser catheter 100 exposes the plurality of optical fibers 120 (see FIGS. 1D-E), which create a peripheral ring between the guidewire lumen 130 and an external sheath of the laser catheter 100. As discussed above, the laser catheter 100 is typically inserted into the blood vessel 136 over the guidewire 132 through the guidewire lumen 130. The distal face 112 of the laser catheter 100 is shown adjacent the vascular obstruction 134 (e.g., thrombosis). Because the plurality of optical fibers 120 are exposed at the distal face 112 of the laser catheter 100, when the distal face 112 of the laser catheter 100 is positioned adjacent to a vascular obstruction 134, the energy emitted from the plurality of optical fibers 120 cuts, separates, penetrates, and/or ablates at least a portion of the vascular obstruction 134. FIG. 1C illustrates the distal end 110 of the laser catheter 100 beyond the remaining portion of the vascular obstruction 134 after the optical fibers 120 within the laser catheter 100 have ablated at least a portion of the vascular obstruction 134.

As the energy emitted by the laser emitters contacts a vascular obstruction 134, the laser can separate, cut, or ablate at least a portion of the vascular obstruction 134. In some cases, fluid comprising one or more thrombolytic agents may exit a fluid delivery lumen 142, contact the vascular obstruction 134, and subsequently circulate back to the catheter and into fluid removal ports 150 coupled to the fluid removal lumen 140 (exemplary fluid flow is represented by dotted arrows in FIG. 1C). In some cases, portions of the vascular obstruction that were separated from the main body of the obstruction may be removed from the vessel through the fluid removal ports 150 coupled to the fluid removal lumen 140. Thus, the fluid removal ports 150 can both function to circulate the fluid and to remove undesirable portions of the vascular obstruction 134 separated after the laser ablation procedure and after exposure to fluid comprising one or more thrombolytic agents.

Generally, performing an ablation procedure on at least a portion of a vascular obstruction causes the denaturing of the proteins (e.g., fibrin) that make up the vascular obstruction. Protein denaturing can expose more of the surface area of obstruction, such that subsequent treatment with a fluid comprising a thrombolytic agent will penetrate deeper into the obstruction. In this way, the combination of ablation and thrombolysis can have a synergetic effect by enabling the removal or dissolution of more of the obstruction in less overall time compared to other conventional means (e.g., ultrasonic ablation). Additionally, the combination of ablation and thrombolysis can reduce the damage to surrounding tissue (e.g., vascular walls) because the additional step of thrombolysis ensures that the ablation procedure does not have to be performed for as long in order to remove the obstruction and, therefore, the surrounding tissues are less likely to be damaged by the ablation procedure. The ablation procedure need only be performed long enough to denature some of the proteins in the obstruction to increase the surface area of the obstruction, not long enough to remove a portion of the obstruction itself.

The laser catheter 100 may also comprise one or more catheter balloons (not shown) located at the distal end 110 of the laser catheter 100, which function to isolate the area of the vessel that surrounds the vascular obstruction 134. For example, the distal end 110 of the catheter may comprise a catheter balloon located proximal to the distal face 112 of the catheter and distal to the fluid delivery ports 170. The distal end 110 of the catheter may also comprise a second catheter balloon located proximal to the fluid removal ports 150. One balloon will, therefore, be disposed on the laser catheter 100 proximally of both the fluid removal ports 150 and the fluid delivery ports 170, and the other balloon will be disposed on the laser catheter 100 distally of both the fluid removal ports 150 and the fluid delivery ports 170, thereby isolating the fluid removal ports 150 and the fluid delivery ports upon inflation of the balloons within the blood vessel. 170 The catheter balloons can be inflated during an ablation and/or thrombolysis procedure such that the catheter balloons create barriers around the vascular obstruction 134. The fluid comprising the one or more thrombolytic agents can then circulate within this isolated area, thus maximizing exposure of the vascular obstruction 134 to the fluid.

Figure 1D:
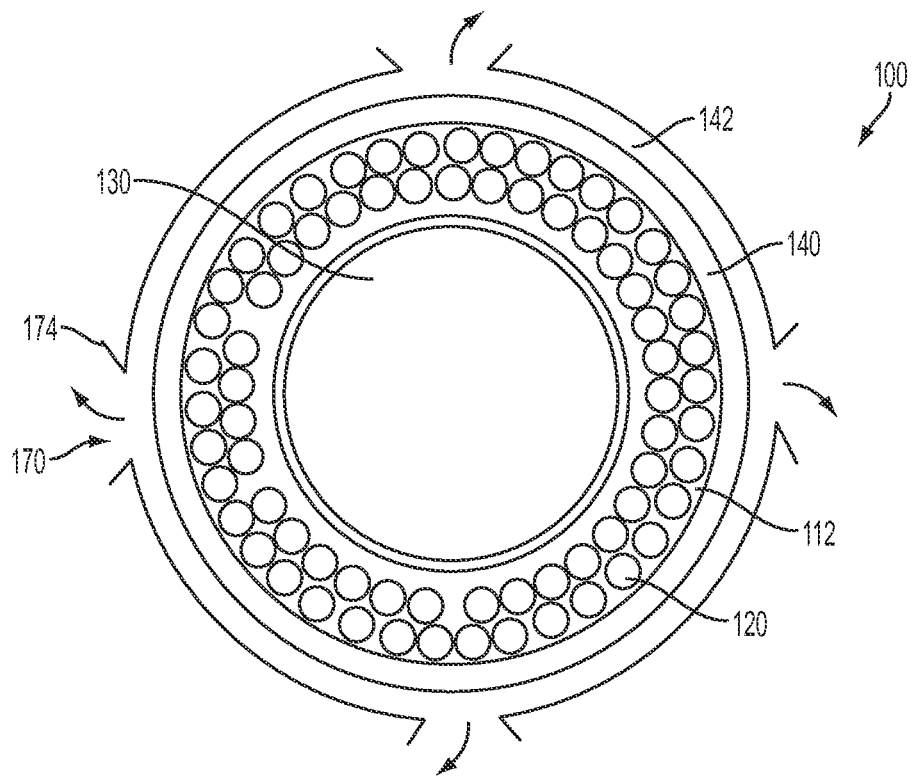
FIG. 1D is a cross-sectional view of the distal end of a laser catheter taken along the entry ports for the fluid evacuation lumen(s), according to an embodiment of the present disclosure.

Referring to FIG. 1D, a cross-sectional view of the distal end 110 of an embodiment of laser catheter 100 taken along the fluid delivery ports 170 for the fluid delivery lumen 142 is shown. Again, the laser catheter 100 may comprise a plurality of optical fibers 120 that extend at least partially from the proximal end 105 (or adjacent thereto) of the laser catheter to the distal end 110 of the laser catheter. The proximal end 105 of the laser catheter may be attached to a coupler 115, such as a fiber optic laser coupler, that connects the fiber optic cables within the laser catheter 100 to the laser source (not shown), such as an excimer laser generator. The plurality of optical fibers 120 may be exposed at the distal face 112 of the laser catheter 112 as shown in FIG. 1D. In some cases, the fluid delivery lumen 142 may be external to the fluid removal lumen 140, as shown in FIG. 1D.

The laser catheter 100 may also comprise one or more fluid delivery ports 170 within the sides of the laser ablation catheter 100 at, near and/or adjacent its distal end 110. The fluid delivery ports 170 are fluidly connected to one or more fluid delivery lumens 142, which in turn are fluidly connected to the fluid delivery port 122 and channel within the fluid connector 116. As shown in FIG. 1C, after the laser catheter 100 has ablated at least a portion of the vascular obstruction 134, when the distal end 110 of the catheter is positioned adjacent to a vascular obstruction, the fluid delivered via the fluid delivery ports 170 can contact the remaining vascular obstruction 134. In some cases, the fluid delivery lumen 142 and/or ports 170 may be sealed and/or waterproofed so that no fluid leaks into the surrounding portions of the laser catheter 100, and so that the fluid delivered is not contaminated before coming into contact with the vascular obstruction. For example, as depicted in FIG. 1D, the fluid delivery ports 170 may be sealed by one or more flaps and or valves 174 that open outwardly upon delivery of the fluid.

Figure 1E:
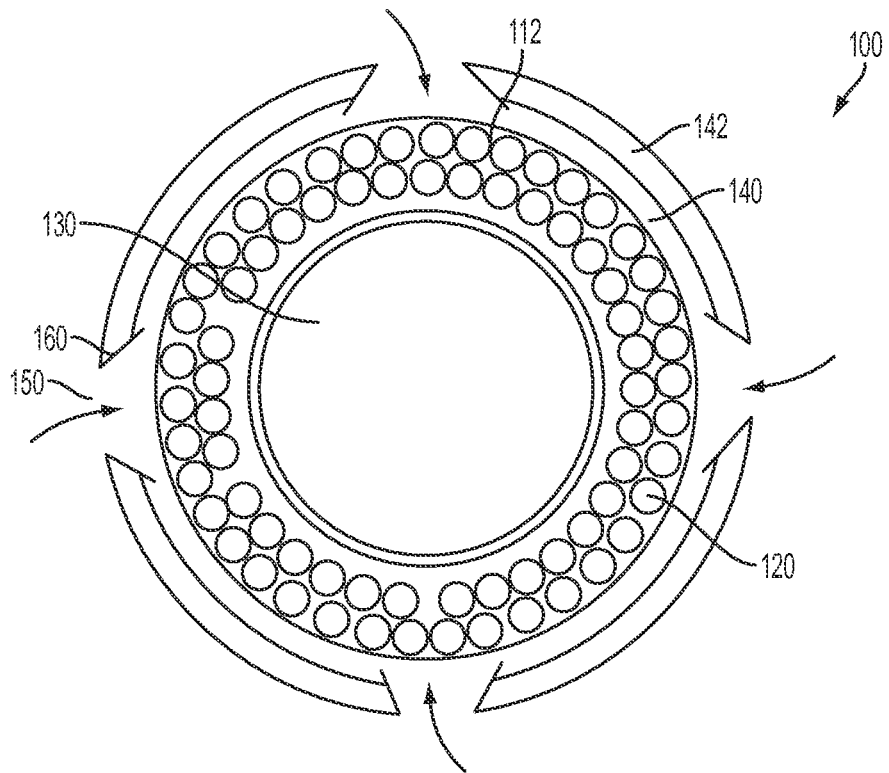
FIG. 1E is a cross-sectional view of the distal end of a laser catheter taken along the exit ports for the fluid deliver lumen(s), according to an embodiment of the present disclosure.

Referring to FIG. 1E, the laser catheter 100 may also comprise one or more fluid removal ports 150 within the sides of the laser ablation catheter 100 at, near and/or adjacent its distal end. The removal ports 150 are fluidly connected to one or more fluid removal lumens 140, which in turn are fluidly connected to the fluid evacuation port 124 and channel within the fluid connector 116. The fluid removal lumen 140 and/or ports 150 may be sealed and/or waterproofed so that no bodily fluid leaks into the removal lumen of the laser catheter 100 before coming into contact with the vascular obstruction. For example, as depicted in FIG. 1E, the fluid removal ports 150 may be sealed by one or more flaps and or valves 160 that open inwardly upon suction of the fluid. The proximal end 105 of the laser catheter 100 may comprise a fluid collector 118 that can be coupled to the fluid removal lumen 140 via the fluid evacuation port 124 within the fluid connector 116. The fluid collector 118 may be continuous with the fluid removal lumen 140, such that when fluid enters the fluid removal ports 150, the fluid flows through the fluid removal lumen 140 until the fluid is deposited in the fluid collector 118. In some cases, the fluid removal lumen 140 may be sealed and/or waterproofed so that no fluid leaks into the surrounding portions of the catheter, or contaminates the fluid delivered through the fluid delivery lumen 142. In some cases, the fluid removal lumen 140 may be external to the fluid delivery lumen 142, as shown in FIG. 1E.

The fluid delivery lumen 142 can be operably coupled to a pump (not shown) that exerts positive pressure on the fluid to facilitate its flow through the fluid delivery ports 170 and out the distal end 110 of the catheter. In some cases, the fluid removal lumen 140 can be operably coupled to a vacuum (not shown) that exerts negative pressure on the fluid to facilitate its flow through the fluid removal ports 150, through the fluid removal lumen 140, and out the fluid collector 118. In some cases, the fluid can be circulated through the fluid delivery lumen 142 and the fluid removal lumen 140 in a coordinated manner, thus facilitating maximum exposure of the vascular obstruction to the fluid.

The fluid delivery ports 170 and the fluid removal ports 150 may occupy various positions within the catheter, depending on the particular application of the laser catheter 100. For example, in some cases, fluid delivery ports may occupy a position surrounding the plurality of optical fibers 120, while fluid removal ports may occupy a centrally located position within the laser catheter. In such embodiments, the fluid may exit the fluid delivery ports on the side of the laser catheter, and subsequently be taken into the fluid removal ports through the distal face of the laser catheter. Alternatively, the fluid may exit the fluid delivery ports through the distal face or guidewire lumen of the laser catheter, and subsequently be taken into the fluid removal ports through the side of the laser catheter. Other various arrangements of the fluid delivery lumen 142 and/or ports, the fluid removal lumen 140 and/or ports and the plurality of optical fibers 120 can readily be constructed by one of skill in the art.

The fluid delivered by the laser catheter 100 may comprise one or more thrombolytic agents. The one or more thrombolytic agents may be used in accordance with the laser catheter 100 to facilitate the removal or dissolving of a vascular obstruction. The one or more thrombolytic agents can include, for example, tissue plasminogen activator (tPA), heparin, alteplase, anistreplase, kabikinase, prourokinase, reteplase, rokinase, streptokinase, tenecteplase and urokinase. In some embodiments, the fluid comprises recombinant tPA (rtPA). In some embodiments, the fluid comprises rtPA and may be administered to a subject at a dosage between about 0.5 and about 1.2 milligrams per kilogram (mg/kg) of the subject's body weight. In other embodiments, the fluid comprises rtPA and may be administered to the subject at a dosage of about 0.9 mg/kg of the subject's body weight.

The thrombolytic agents currently available generally include serine proteases that work by converting plasminogen to the natural fibrinolytic agent plasmin. Plasmin lyses clots by breaking down the fibrinogen and fibrin contained in a clot. Tissue plasminogen activator (tPA) is a naturally occurring fibrinolytic agent found in vascular endothelial cells and is involved in the balance between thrombolysis and thrombogenesis. It exhibits significant fibrin specificity and affinity. At the site of a thrombus, for example, the binding of tPA and plasminogen to the fibrin surface induces a conformational change that facilitates the conversion of plasminogen to plasmin and dissolves the clot. Fibrinolytic agents, sometimes referred to as plasminogen activators, can generally be divided into 2 categories: Fibrin-specific agents, and Non-fibrin-specific agents.

Fibrin-specific agents, which include alteplase (tPA), reteplase (recombinant plasminogen activator (r-PA)), and tenecteplase, produce limited plasminogen conversion in the absence of fibrin. Non-fibrin-specific agents (eg, streptokinase) catalyze systemic fibrinolysis. Streptokinase is indicated for the treatment of acute myocardial infarction, acute massive pulmonary embolism (PE), deep vein thrombosis (DVT), arterial thrombosis, and occluded arteriovenous cannulae.

Reteplase is a recombinant tissue-type plasminogen activator that studies suggest works more rapidly and provides a lower bleeding risk than other agents (e.g., alteplase). It is a synthetic nonglycosylated deletion mutein of tPA that contains 355 of the 527 amino acids of native tPA. Reteplase can be produced in *Escherichia coli* by means of recombinant DNA techniques. Because reteplase does not bind fibrin as tightly as native tPA does, it can diffuse more freely through the clot rather than bind only to the surface as tPA does. At high concentrations, reteplase does not compete with plasminogen for fibrin-binding sites, allowing plasminogen at the site of the clot to be transformed into clot-dissolving plasmin. These characteristics help explain why clots resolve faster in patients receiving reteplase than in those receiving alteplase, for example.

Tenecteplase is a recently described thrombolytic agent approved for use in clinical practice by the FDA as a fibrinolytic agent in 2000. It can be produced by recombinant DNA technology using Chinese hamster ovary cells, for example. Its mechanism of action is similar to that of alteplase, and it is currently indicated for the management of acute myocardial infarction. Tenecteplase is a 527-amino-acid glycoprotein (GP) that sustained several modifications in amino acid molecules. These modifications give tenecteplase a longer plasma half-life and greater fibrin specificity. In addition, these modifications allow single-bolus administration and yield decreased bleeding side effects as a consequence of the high fibrin specificity.

Fibrinolytic agents can be administered systematically or can be delivered directly into the area of the thrombus. Systemic delivery is used for treatment of acute myocardial infarction, acute ischemic stroke (AIS), and most cases of acute massive PE. Peripheral arterial thrombi and thrombi in the proximal deep veins of the leg are most often treated via a catheter-directed approach. Alteplase is the only lytic agent currently approved by the US Food and Drug Administration (FDA) for acute myocardial infaction, acute ischemic stroke, massive PE, and occluded central venous access devices (CVADs). Additional agents and different dosing regimens are under constant investigation. The choice of a lytic agent must be based both on the results of ongoing clinical trials and on the clinician's experience. The most appropriate agent and regimen for each clinical situation will change over time and may differ from patient to patient.

The distal end of the laser catheter 100 can be structured to create a closed circulating system. For example, fluid may be released from the fluid delivery lumen 142 and fluid deliver ports 170 for a predetermined amount of time, after which the fluid removal ports 150 may be opened, such that the fluid enters the fluid removal lumen 140 instead of the fluid removal lumen 140, and circulates back out of the proximal end of the laser catheter. In such cases, the flaps 174, 160 may be structured to open directly into the fluid delivery lumen 142 and fluid removal lumen 140, respectively. Additionally, in such embodiments, the continuous delivery of fluid from the proximal end of the catheter (e.g., the fluid source) may be shut off to create a closed circulating system, or fresh fluid may continually be delivered to create a partially closed circulating system.

Although FIGS. 1A-E illustrate a generally concentric configuration of the plurality of optical fibers, the fluid delivery lumen, and the fluid removal lumen, those skilled in the art will appreciate that there are numerous other ways and configurations in which to arrange these various components. Accordingly, FIGS. 1A-E are not intended to represent the only way that a laser catheter may be configured and constructed, and all such configurations and constructions are within the knowledge of one skilled in the art are considered within the scope of this disclosure. For example, embodiments of the present disclosure contemplate various mechanical cutting features provided in combination with a catheter, either in addition to or in lieu of laser ablation means. Such mechanical cutting features include, but are not limited to, various bladed or shearing devices provided at or proximal to a distal end of the catheter. Such mechanical cutting features are contemplated as being substantially fixed to a distal end of a catheter, such as the periphery of an annular distal end, or selectively retractable/extendable from the distal end such that the cutting features are only provided in a position of use when desired.

Figure 2:
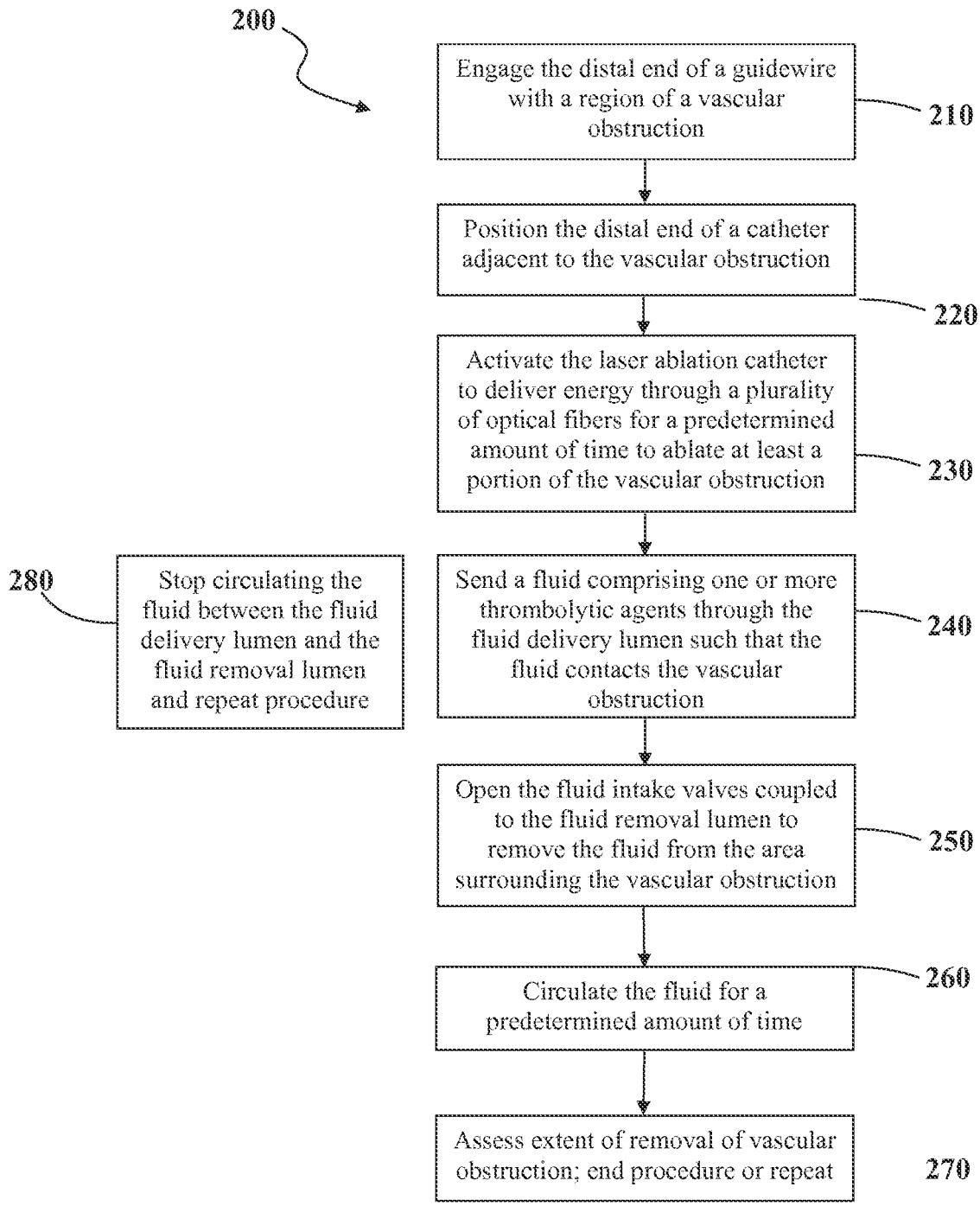
FIG. 2 is a flow chart representing a method for performing laser assisted thrombolysis using the laser catheter, according to an embodiment of the present disclosure.

Referring to FIG. 2, a flow chart representing a method for performing laser assisted thrombolysis using the laser catheter 100 is shown. In certain embodiments, the method of performing laser assisted thrombolysis according to the present disclosure comprises the initial step 210 of engaging the distal end of a guidewire 132 with a region of a vascular obstruction 134. Next, at step 220, the distal end of a laser catheter may be positioned adjacent to the vascular obstruction (e.g., a working distance from the obstruction). Next, at step 230, the laser catheter may be activated to deliver energy through a plurality of optical fibers (see FIGS. 1A-E) for a predetermined amount of time in order to ablate at least a portion of the vascular obstruction. For example, the ablation may be conducted for between about 1 minute and about 15 minutes. In some embodiments, the ablation may be conducted for between about 2 minutes and about 10 minutes. In some embodiments, the ablation may be conducted for between about 5 minutes and about 10 minutes. In some embodiments, the ablation may be conducted for between about 5 minutes and about 8 minutes. In still other embodiments, the ablation may be conducted for about 1, 2, 3, 4, 5, 6, 7, 8, 9 or 10 minutes.

Next, at step 240, a fluid can be pumped into the fluid delivery port 122 of the fluid connector 116 and be sent through the fluid delivery lumen 142 such that the fluid exits the fluid delivery ports 170 within the laser catheter, thereby contacting the vascular obstruction, or a remaining portion of the vascular obstruction. The fluid can be delivered from a fluid source, through the fluid delivery lumen, until it exits the distal end of the laser catheter (see FIGS. 1A-E). In some embodiments, the fluid comprises one or more thrombolytic agents to facilitate the removal or dissolving of a vascular obstruction. The one or more thrombolytic agents can include, for example, tissue plasminogen activator (tPA), heparin, alteplase, anistreplase, kabikinase, prourokinase, reteplase, rokinase, streptokinase, tenecteplase and urokinase. In some embodiments, the fluid comprises recombinant tPA (rtPA). In some embodiments, the fluid comprises rtPA and may be administered to a subject at a dosage between about 0.5 and about 1.2 mg/kg of the subject's body weight. In other embodiments, the fluid comprises rtPA and may be administered to the subject at a dosage of about 0.9 mg/kg of the subject's body weight.

Next, at step 250, fluid removal ports 150 coupled to the fluid removal lumen 140 can be opened to evacuate the fluid after it has contacted the vascular obstruction for a predetermined time. The fluid can enter the intake valves, travel through the fluid removal lumen 140, and exit the laser catheter (see FIGS. 1A-E). Both the fluid and portions of the vascular obstruction that may have been separated from the main obstruction after laser ablation may be removed from the area surrounding the obstruction through the fluid removal lumen 140. Next, at step 260, the laser catheter can be operated to circulate the fluid between for a predetermined amount of time (see FIGS. 1A-E). For example, the fluid may be circulated for between about 10 minutes and about 100 minutes. In some embodiments, the fluid may be circulated for between about 10 minutes and about 80 minutes. In some embodiments, the fluid may be circulated for between about 10 minutes and about 60 minutes. In some embodiments, the fluid may be circulated for between about 20 minutes and about 60 minutes. In some embodiments, the fluid may be circulated for between about 20 minutes and about 40 minutes. In some embodiments, the fluid may be circulated for between about 30 minutes and about 40 minutes. In still other embodiments, the fluid may be circulated for about 10, 15, 20, 25, 30, 35, 40, 45, 50, 55 or 60 minutes.

Next, at step 270, the extent of the removal or dissolving of the vascular obstruction may be assessed in order to determine whether the procedure is complete, or whether the procedure should be repeated, as described at 280.

Optionally, the method for performing laser assisted thrombolysis using the laser catheter 100 may also comprise inflating one or more catheter balloons located at the distal end 110 of the laser catheter 100, which function to isolate the area of the vessel that surrounds the vascular obstruction 134. For example, one or more catheter balloons can be inflated during an ablation and/or thrombolysis procedure such that the catheter balloons create barriers around a vascular obstruction. The fluid comprising the one or more thrombolytic agents can then circulate within this isolated area, thus maximizing exposure of the vascular obstruction to the fluid.

The method of performing laser assisted thrombolysis using the laser ablation laser catheter described herein may comprise performing the laser ablation procedure prior to performing thrombolysis. In some embodiments, the method may comprise performing thrombolysis prior to performing the laser ablation procedure. In some embodiments, the method may comprise simultaneously performing the laser ablation procedure and thrombolysis. In still other embodiments, the method may comprise various combinations and orders of performing the laser ablation procedure and thrombolysis, as determined by one of skill in the art.

EXAMPLES

The present disclosure is more particularly described in the following examples that are intended as illustrations only, since numerous modifications and variations within the scope of the present disclosure will be apparent to those of skill in the art.

Example 1: The Combined Effects of Using Laser Thrombolysis Therapy and Pharmacological Thrombolysis to Treat Venous Thrombotic Obstructions FIG. 3 is a graphical representation illustrating the reduction in the average size of thrombi after treatment with both laser ablation therapy and a recombinant tissue plasminogen activator (rtPA), as compared to treatment with recombinant rtPA alone.

Thrombi were generated using the Chandler Loop System. About 2 mLs of blood was obtained from healthy volunteers and introduced into polyvinylchloride tubing, roughly 40 cm in length and 3.2 mm in diameter. Coagulation was initiated by adding 20 μl of 0.05 UI/μL human thrombin. Each tube was immediately closed to form a circle ("loop") and placed in a rotating water basin at 34° C. for 30 minutes to produce the thrombi. Subsequently, each tube was placed at an incline and opened at one end to allow for laser ablation treatment of a subset of the samples. Laser ablation was applied for five minutes (1 cm/min) at 30-80 mJ/mm$^2$. The temperature of each sample was then recorded. After laser ablation treatment, 5 mg Actilyse (a tissue plasminogen activator produced from recombinant DNA) was introduced into a subset of the samples and allowed to incubate for a total of 30 minutes. The samples were then transferred to canonical tubes for centrifugation and removal of plasma for later analysis (e.g., detection of D-dimer, fibrin factor XIII, fibrinogen gamma, and plasminogen). The remaining red blood cells were decanted, the thrombi were briefly washed, and then weighed.

Samples receiving neither laser ablation treatment nor Actilyse were used as untreated controls ("Control"). The experimental samples received either Actilyse alone ("rtPA Lysis") or Actylise with laser ablation treatment ("rtPA Lysis+Laser"). A total of six samples were tested for each of these sample groups. Average thrombi size was calculated for each group (±standard deviation).

Figure 3:
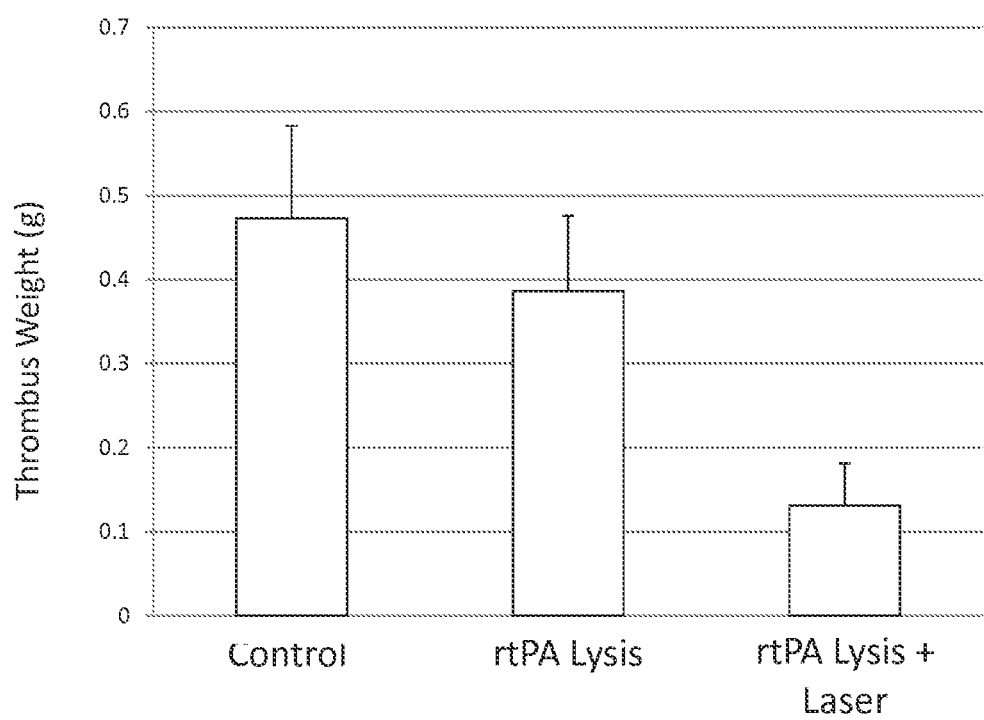
FIG. 3 is a graphical representation illustrating the effects of laser assisted thrombolysis on average thrombus size, according to an embodiment of the present disclosure.

As shown in FIG. 3, the average weight of thrombi receiving both Actilyse and laser ablation treatment was significantly lower than the thrombi receiving Actilyse alone. The average thrombus weight for the Control group was 0.473±0.011. The average weight of the rtPA Lysis group was 0.386±0.09. And the average thrombus weight of the rtPA Lysis+Laser group was 0.131±0.05 (p=0.027 for the rtPA Lysis group compared to the rtPA Lysis+Laser group). Table 1 below summarizes the results of this experimental analysis. Notably, the combination of Actilyse and laser ablation completely eliminated the thrombus in two of the six samples in that group.

TABLE 1

Results comparing the effects of laser ablation therapy and thrombolysis on thrombus weight.

| Group | Sample No. | Time Lysis (min.) | Time Laser (min.) | Temp. ° C. | Weight (g) |
|---|---|---|---|---|---|
| Control | 1 | 0 | 0 | 34.3 | —//— |
|  | 2 | 0 | 0 | 34.3 | 0.507 |
|  | 3 | 0 | 0 | 34.3 | 0.473 |
|  | 4 | 0 | 0 | 34.3 | 0.764 |
|  | 5 | 0 | 0 | 34.3 | 0.653 |
|  | 6 | 0 | 0 | 34.3 | 0.441 |
| rtPA Lysis | 1 | 30 | 0 | 34.3 | 0.603 |
|  | 2 | 30 | 0 | 34.3 | 0.213 |
|  | 3 | 30 | 0 | 34.3 | 0.637 |
|  | 4 | 30 | 0 | 34.3 | 0.293 |
|  | 5 | 30 | 0 | 34.3 | 0.410 |
|  | 6 | 30 | 0 | 34.3 | 0.161 |
| rtPA Lysis + Laser (30/80) | 1 | 30 | 5 | 36.3 | 0.169 |
|  | 2 | 30 | 5 | 37.0 | 0.000 |
|  | 3 | 30 | 5 | 37.1 | 0.236 |
|  | 4 | 30 | 5 | 36.8 | 0.125 |
|  | 5 | 30 | 5 | 36.5 | 0.231 |
|  | 6 | 30 | 5 | 36.9 | 0.000 |

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of treating thrombosis in a subject, the method comprising:
    positioning a catheter within a vessel of a subject, wherein the catheter comprises a proximal end, a distal end, a plurality of optical fibers, a fluid delivery lumen and a fluid removal lumen, at least one fluid delivery port coupled to the fluid delivery lumen and disposed adjacent and exteriorly the distal end, and at least one fluid removal port coupled to the fluid removal lumen and disposed adjacent and exteriorly the distal end, wherein the distal end comprises a distal face, wherein the plurality of optical fibers extend through at least a portion of the catheter to the distal face, wherein the plurality of optical fibers are exposed at the distal face, and wherein the distal end of the catheter is positioned adjacent an obstruction in the vessel;
    ablating at least a portion of the obstruction by delivering laser energy through the plurality of optical fibers to the distal face of the catheter for between 2 minutes and 10 minutes;
    circulating a fluid to a remaining portion of the obstruction for between 20 minutes and 40 minutes, wherein the fluid circulates through the fluid delivery lumen, exits the fluid delivery port, and returns through the fluid removal port to the fluid removal lumen, the fluid comprising one or more thrombolytic agents.

2. The method of claim 1, wherein ablating at least a portion of the obstruction occurs prior to circulating the fluid.

3. The method of claim 1, wherein ablating at least a portion of the obstruction occurs simultaneously with circulating the fluid.

4. The method of claim 1, wherein the ablation procedure occurs for about 5 minutes.

5. The method of claim 1, wherein the fluid is in contact with the remaining portion of the obstruction for about 30 minutes.

6. The method of claim 1, wherein the one or more thrombolytic agents includes tissue plasminogen activator, heparin, urokinase, streptokinase, kabikinase, anistreplase, reteplase, tenecteplase and rokinase.

7. The method of claim 1, wherein the one or more thrombolytic agents is tissue plasminogen activator administered to the subject at a dosage between about 0.5 and about 1.2 milligrams per kilogram of the subject's body weight.

8. The method of claim 1, wherein the one or more thrombolytic agents is tissue plasminogen activator administered to the subject at a dosage of about 0.9 milligrams per kilogram of the subject's body weight.

9. A system for treating thrombosis in a subject, the system comprising:
    a laser ablation catheter comprising:
        a proximal end,
        a distal end,
        a sidewall extending between the proximal end and the distal end,
        a guidewire lumen disposed within the sidewall and extending between the proximal end and the distal end,
        a fluid delivery lumen disposed within the sidewall,
        at least one fluid delivery port coupled to the fluid delivery lumen and disposed on the sidewall proximal to the distal end,
        a fluid removal lumen disposed within the sidewall,
        at least one fluid removal port coupled to the fluid removal lumen and disposed on the sidewall proximal to the distal end,
        a plurality of optical fibers, wherein the distal end comprises a distal face, wherein the plurality of optical fibers extend through at least a portion of the catheter to the distal face, and wherein the plurality of optical fibers are exposed at the distal face of the catheter;
    wherein the distal end of the catheter is positioned adjacent to an obstruction in a vessel of a subject to facilitate ablation of at least a portion of the obstruction by delivering laser energy through the plurality of optical fibers to the distal face; and
    wherein a fluid comprising one or more thrombolytic agents circulates through the fluid delivery lumen, exits the fluid delivery port, and returns through the fluid removal port to the fluid removal lumen such that it contacts a remaining portion of the obstruction for a predetermined amount of time.

10. The system of claim 9, wherein ablating at least a portion of the obstruction occurs prior to circulating the fluid.

11. The system of claim 9, wherein ablating at least a portion of the obstruction occurs simultaneously with circulating the fluid.

12. The system of claim 9, wherein the ablation procedure occurs for between about 2 minutes and about 10 minutes.

13. The system of claim 9, wherein the ablation procedure occurs for about 5 minutes.

14. The system of claim 9, wherein the fluid is in contact with the remaining portion of the obstruction for between about 10 minutes and about 60 minutes.

15. The system of claim 9, wherein the fluid is in contact with the remaining portion of the obstruction for about 30 minutes.

16. The system of claim 9, wherein the one or more thrombolytic agents includes tissue plasminogen activator (tPA), heparin, alteplase, anistreplase, kabikinase, prourokinase, reteplase, rokinase, streptokinase, tenecteplase and urokinase.

17. The system of claim 9, wherein the one or more thrombolytic agents is tissue plasminogen activator administered to the subject at a dosage between about 0.5 and about 1.2 milligrams per kilogram of the subject's body weight.

18. The system of claim 9, wherein the one or more thrombolytic agents is tissue plasminogen activator administered to the subject at a dosage of about 0.9 milligrams per kilogram of the subject's body weight.

* * * * *